United States Patent
Pullman

(10) Patent No.: US 6,893,873 B2
(45) Date of Patent: May 17, 2005

(54) METHODS FOR IMPROVING CONIFER EMBRYOGENESIS

(75) Inventor: Gerald S. Pullman, Alpharetta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 6 days.

(21) Appl. No.: 10/351,491

(22) Filed: Jan. 27, 2003

(65) Prior Publication Data

US 2003/0153080 A1 Aug. 14, 2003

Related U.S. Application Data

(60) Provisional application No. 60/350,944, filed on Jan. 25, 2002.

(51) Int. Cl.$^7$ ............................................... C12N 5/00
(52) U.S. Cl. ............................................ 435/422
(58) Field of Search ..................................... 435/422

(56) References Cited

U.S. PATENT DOCUMENTS 5,464,769 A 11/1995 Attree et al.

OTHER PUBLICATIONS

Bio–World– molecular tools & laboratory essentials, [online] Retrieved on Apr. 8, 2004, http://www.bio–world.com.*

Huang, L. et al., "Plant Tissue Culture Media: Major Constituents, Their Preparation and Some Applications," Tissue Culture Assoc., 1997, Manual 3, 539–548.*

Gamborg, O.L., et al., "Nutrition, Media and Characteristics of Plant Cell and Tissue Cultures," 1981, Academic Press, 21–44.*

Nelson, D., et al., "Lehninger Principles of Biochemistry," Worth Publishers, Third Edition, p. 572.*

Svobodova, H., et al., "Somatic embryogenesis in Norway spruce: Anatomical study of embryo development and influence of polyethylene glycol on maturation process," Plant Physiol. Biochem., 1999, 37 (3), 209–221.*

Hakman, et al., The Development of Somatic Embryos in Tissue Cultures Initiated From Immature Embryos of *Picea Abies* (Norway Spruce), *Plant Science*, 38 (1985), pp. 53–59.

Hakman, et al., Plantlet Regeneration through Somatic Embryogenesis in *Picea abies* (Norway Spruce), *J. Plant Physiol.*, vol. 121, (1985), pp. 149–158.

* cited by examiner

*Primary Examiner*—Bruce R. Campell
*Assistant Examiner*—S. B. McCormick-Ewoldt
(74) *Attorney, Agent, or Firm*—Troutman Sanders LLP; Ryan A. Schneider

(57) ABSTRACT

The present invention provides methods for initiating, capturing, maintaining and multiplying embryogenic cultures of coniferous plants. Methods include the use of novel media compositions containing Vitamin $B_{12}$, Vitamin E, or organic acids including α-ketoglutaric acid, pyruvic acid, or p-aminobenzoic acid to improve the frequency of embryogenic tissue initiation, capture, maintenance and multiplication. The methods are well suited for initiating embryogenic cultures in recalcitrant conifer varieties. The method is also well suited for producing somatic embryos that can be further cultured to produce large numbers of plants. Further, the invention provides novel methods that may be used to enhance somatic embryogenesis in a broad range of species.

32 Claims, No Drawings

METHODS FOR IMPROVING CONIFER EMBRYOGENESIS

CROSS-REFERENCE TO RELATED APPLICATIONS

This patent application claims benefit of priority of provisional application U.S. Ser. No. 60/350,944, filed Jan. 25, 2002.

FIELD OF THE INVENTION

The present invention is directed to methods for improved somatic embryogenesis in conifers and, particularly, in loblolly pine. Methods and compositions of media are provided for promoting initiation of conifer explants, improving maintenance and increasing the yield of conifer embryo multiplication. The methods comprise providing culture medium supplemented with vitamin $B_{12}$, vitamin E, the K&M vitamin mixture, organic acids, such as, for example, TCA cycle acids and p-aminobenzoic acids, or a combination of these vitamins and acids. The methods are also useful for more efficient capture of previously initiated embryogenic tissue.

BACKGROUND OF THE INVENTION

Implementation of clonal tree production is a major step that will be taken by the forest products industry in coming years. Clonal deployment of advance generation selections is expected to increase forest productivity by some 10% to 20% and increase uniformity of the fiber output (Libby et al., For. Chron. 60:145–149 (1984)). Significant economic and biological barriers exist to large-scale clonal propagation and plantation of softwood trees (Stelzer et al., Can. J. For. Res. 27:442–446 (1997)). For many softwood trees including loblolly pine, somatic embryogenesis is the most promising method to overcome these barriers (Cheliak et al., Can. J. For. Res. 20:452–463 (1990)). Somatic embryogenesis is widely used in a variety of plant species to produce multiple copies of genetically identical organisms. Somatic embryogenesis is becoming the method of choice for clonal propagation of spruce. However, for loblolly pine, the most important species in the United States, somatic embryogenesis has lagged behind.

In some species, somatic embryogenesis is used to propagate desirable plant genotypes. In many crop species, somatic embryogenesis is used to propagate whole transformed plants from tissues that have been genetically altered. Somatic embryogenesis protocols have been developed for the reproduction of conifers. For example, U.S. Pat. Nos. 4,957,866, 5,034,326, 5,036,007, 5,236,841, 5,413,930, 5,491,090, and 5,506,136 (the disclosures of which herein incorporated by reference), describe various methods and media for conifer embryogenesis.

Somatic embryogenesis is a multi-step process by which an individual plant is clonally propagated. Tissue from the parent plant is induced to form embryos. Subsequent culturing steps are then performed to induce the embryos to mature into plantlets. These small plants are capable of growing into mature plants, each of which is genetically identical to the parent. Using this process, an individual plant with a desirable genotype can be efficiently reproduced In conifers, somatic embryogenesis begins with "initiation," the initial formation of embryogenic cultures. Embryogenic cultures contain one or more immature somatic embryos. Initiation is traditionally followed by a maintenance and multiplication phase in which large numbers of clones of the initiated somatic embryo(s) are produced. The embryos produced in the maintenance and multiplication step(s) are then further cultured on a development or maturation media. This development medium induces the immature embryos to mature into late-stage embryos capable of germination. These mature embryos are often placed on a germination medium where they germinate to form plantlets. The plantlets can be grown and acclimated to the point that they are capable of being planted in soil. Subsequently these small plantlets will grow into mature trees.

Many conifer species contain recalcitrant genotypes not readily regenerated. The commercially important loblolly pine, for example, is generally difficult to propagate by somatic embryogenesis (Becwar et al., Can. J. For. Res. 20:810 (1990), Jain et. al., Plant Sci. 65:233–241 (1989)). Further, genetic transformation techniques used to generate transgenic conifers, such as Agrobacterium-mediated gene transfer, electroporation, and particle bombardment, can damage plant cells. Damaged cells are less likely to regenerate into whole plants. Thus, there is a need in the art for methods and compositions that improve the efficiency of somatic embryogenesis, including somatic embryogenesis in conifers.

Initiation of Embryogenic Cultures

Somatic embryogenesis begins with the "initiation" step. Initiation starts with the selection of a suitable explant, that is any plant cell, tissue or organ capable of forming an embryogenic culture. A typical explant in conifer somatic embryogenesis is the megagametophyte, also called the ovule or the female gametophyte, which is extracted from a pollinated female cone and which may contain single or multiple zygotic seed embryos. One or more cells of the explant are then induced to proliferate into a tissue mass containing at least one early stage somatic embryo. The successful establishment of such a culture is known as initiation.

The cultures can be initiated from several types of explants. Most commonly, conifers embryogenic cultures are initiated from zygotic embryos or zygotic embryogenic tissues found in seeds. When intact conifer megagametophytes are used as the explant, the somatic embryogenesis process comprises a distinct step called extrusion. Extrusion is the process in which a mass of embryogenic tissue is extruded from the micropylar end of the megagametophyte when it is placed on or in suitable culture media.

Successfully initiating embryogenic cultures require proper medium and culturing conditions. In conifers, an embryogenic culture is successfully initiated when the zygotic embryo or zygotic embryogenic tissue mass, which has been either extruded or physically removed from a megagametophyte, undergoes division and proliferation. A successfully initiated culture consists of a whitish translucent mucilaginous tissue mass that contains pre-embryonal cells, filamentous suspensor-like cells, and early stage somatic embryos. In a successfully initiated culture, new somatic embryos can often be seen growing directly from older zygotic embryos. Visualization of initiation is aided by the fact that zygotic embryos, as well as extruded tissues, often become brown while initiated tissues are whiter and more translucent. Initiated cultures contain from one to dozens of somatic embryos. In culture, initiation frequency is scored for each dish by counting the number of explants that had successfully initiated embryogenic cultures. Initiation is considered successful when at least one somatic embryo is visible. The appearance of at least two somatic embryos provides a useful confirmation of successful initiation.

Maintenance and Multiplication of Embryogenic Cultures

In conifer somatic embryogenesis, initiation is generally followed by one or more "maintenance and multiplication" steps. Some protocols consist of several maintenance and multiplication steps, each with its own media and culturing conditions. Other protocols utilize a single maintenance and multiplication step. "Maintenance" refers to the preservation of cultures by keeping them alive and viable through continuous growth. "Multiplication" refers to the proliferation of such cultures to provide numerous somatic embryos. Regardless of whether the steps are separate or combined into a single culturing step, this phase of somatic embryogenesis requires that previously initiated embryogenic cultures survive and proliferate, continuously producing viable immature somatic embryos. This requires the proper media and culture conditions.

Various methods of maintaining and multiplying cultures have been described. In some protocols, initiated cultures are grown using a single medium composition prior to transfer to a development and maturation media. For example, U.S. Pat. No. 5,563,061 describes a method for conifer somatic embryogenesis wherein initiated embryogenic cultures are transferred to a single maintenance and multiplication medium where they are cultured to increase the number and size of the embryos. After culturing on this maintenance and multiplication media, the somatic embryos are transferred to maturation and development media. Notably, however, the development, maturation, and germination steps of somatic embryogenesis are not 100% efficient. In order for this protocol to be used effectively, a very large number of somatic embryos must be produced initially.

U.S. Pat. No. 5,491,090 describes methods of somatic embryogenesis where initiated cultures are transferred to a liquid maintenance culture. This patent additionally describes a protocol where embryogenic cultures are initiated on a first media, transferred to a second media, and thereafter transferred to a liquid media for rapid multiplication. The use of a liquid culture is especially advantageous in that handling liquid cultures is much less labor-intensive than manipulating cultures on solid media. This ease of handling makes liquid culture practical for a large-scale production of seedlings via somatic embryogenesis. Very large amounts of somatic embryos can be efficiently produced in liquid cultures, with cultures multiplying as much as 2–6 times weekly. However, the inventors have observed that tissue transferred to liquid culture often does not survive and proliferate. Thus, there is a need in the art for methods that will increase the efficiency of embryogenic culture multiplication using liquid media.

The success of the maintenance and multiplication step is vital for the ultimate generation of plantlets. Embryogenic cultures, once successfully initiated, must proliferate and supply sufficient numbers of somatic embryos such that a reasonable number will ultimately be converted to plantlets. There is a need in the art for methods which improve the growth of embryogenic cultures such that large numbers of somatic embryos may be produced. Further, methods which improve the growth of embryogenic cultures will save time and reduce production costs by more rapidly producing the desired numbers of embryos. Additionally, efficient methods of maintaining and multiplying embryogenic cultures can reduce the number of culturing steps, greatly reducing the time and expenses of the propagation process.

DETAILED DESCRIPTION OF THE INVENTION

The present invention provides methods for increasing the efficiency of conifer somatic embryogenesis. By promoting culture initiation to form a tissue mass, and promoting the subsequent growth and multiplication of the initiated tissue mass. Thus, one embodiment of the invention provides methods for increasing the efficiency of the culture initiation, maintenance and multiplication phases of somatic embryogenesis. Another embodiment of the invention provides methods for improved somatic embryo capture.

Many embodiments of the invention comprise the use of various media compositions. By "use," the inventors refer to the process of placing cultured tissues on or in a liquid, semi-solid, or solidified culture medium. The invention is not limited to media of any consistency and encompasses the use of media ranging from liquid to solid.

Where embodiments of the invention comprise the use of organic acids as additives to the culture medium, for instance, acetic, p-aminobenzoic, ascorbic, adipic, alpha-ketoglutaric, alpha-resorcylic, azelaic, benzoic, beta-hydroxybutyric, butyric, butanoic, caffeic, chelidonic, chlorogenic, cinnamic, citric, cis-acontic, citramalic, coumaric, ethylmalonic, ferulic, formic, fumaric, gallic, glutaric, glutaconic, glucuronic, gluconic, glyceric, glycolic, glyoxylic, humic, 4-hydroxycinnamic, 2-hydroxyisobutyric, 3,5-dihydroxybenzoic, 3,4-dihydroxycinnamic, 4-hydroxybenzoic, 2,6-dihydroxybenzoic, 3-hydroxybenzoic, 2,4-dihydroxybenzoic, 3,4-dihydroxybenzoic, 4-hydroxy-3-methoxybenzoic, trans-4-hydroxy-3-methyl cinnamic, 2-hydroxycinnamic, isocitric, isophthalic, lactic, maleic, malic, malonic, methanesulfonic, 3,5-dimethoxy-4-cinnamic, methylmalonic, oxalacetic, oxalic, phthalic, pimelic, propionic, protocatechic, 2-pyrrolidone-5-carboxylic, pyroglutamic, pyruvic, quinic, quinolic, salicylic, sebacic, shikimic, sinapic, sorbic, suberic, succinic, syringic, tartaric, terephthalic, vanillic, the acids can be substituted by their respective salt forms to achieve functional equivalency. The term "TCA cycle acids" refers to those organic acids involved in the tricarboxylic acid cycle, also known as, the Kreb's Cycle. Examples of the TCA cycle acids include alpha-ketoglutaric, oxaloacetic, fumaric, succinic, malic, oxalic, citric and isocitric acids. A person skilled in the art will appreciate that other organic acids ubiquitous in plant tissue may be successfully used in the embodiments of the invention.

An "embryo," depending on its stage of development, will have a variable morphology. Stages 1–9.10 as defined by Pullman and Webb, TAPPI R&D Division 1994 Biological Sciences Symposium, pp 31–34, which is hereby incorporated by reference, define embryos at different points of development. Development spans from Stage 1, where embryos are composed of 12 or less cells to Stage 9.10 where embryos are well developed and have accumulated their full mature weight.

"Embryogenic tissue" in conifer is a translucent white mucilaginous mass that contains early stage embryos and suspensor-like cells, and may contain small, dense globular clusters of cells capable of forming somatic embryos.

An "explant" is the organ, tissue, or cells derived from a plant and cultured in vitro for the purpose of starting a plant cell or tissue culture.

"Extrusion" is the process by which zygotic embryos and/or embryogenic tissue derived from zygotic embryos emerges or extrudes from the corrosion cavity of the megagametophyte of conifer seeds via the opening in the micropylar end, when placed in culture.

"Gamete" refers to a mature reproductive cell which is capable of fusing with a cell of similar origin but of opposite sex to form a zygote from which a new organism can develop. Gametes have a haploid chromosome content and in plants, gametes are pollen, spermatic nucleous, or ovum.

"Germination" refers to the initial stages in the growth of a seed to form a seedling. The embryonic shoot (plumule) and embryonic root (radicle) emerge and grow upwards and downwards respectively. This final stage of embryonic development represents the ability to transition from tissue culture to eventual field plantings.

"Genotype" refers to the particular genetic composition of an organism.

"Initiation" is the initial cellular proliferation and development of zygotic tissues to form a culture containing somatic embryos.

"Maturation" refers to the cellular transition from early-stage to late-stage embryos and ultimately to germination.

A "megagametophyte" is haploid nutritive tissue of the conifer seed, of maternal origin, within which the conifer zygotic embryos develop.

"Nutrients" are the inorganic nitrogen, inorganic minerals, vitamins, organic supplements, and carbon sources necessary for the nourishment of the culture.

A "plantlet" is a small germinating plant asexually reproduced by tissue culture. A plantlet is that which is usually produced vegetatively from a parent plant.

"Somatic" refers to vegetative or non-sexual stages of a life-cycle and a "somatic cell" refers to any cell of a multicellular organism that composes the body of that organism but does not produce gametes.

A "somatic embryo" refers to those embryos produced either from somatic cells of explants (direct embryogenesis) or by induction on callus formed by explants (indirect embryogenesis), which can also be referred to as asexual embryogenesis.

"Somatic embryogenesis" is the process using tissue culture techniques for generating multiple embryos from an explant. The embryos generated from a given tissue source are believed to be genetically identical.

A "zygotic embryo" is an embryo(s) that is derived from the sexual fusion of gametes during pollination and is found within the megagametophyte.

Methods for Improving Embryogenic Culture Initiation

The goal of culture initiation is to create embryogenic tissue that is capable of proliferation. Culture initiation begins when cells from the explants are induced to divide and differentiate into embryogenic cells. These cells must retain the ability to continue replicating. Methods of the invention increase the frequency of successful initiation overall. The factors disclosed below may promote differentiation of cells into those with an embryogenic identity. Alternatively, these factors may increase the robustness of newly formed embryogenic cells such that they more frequently survive or more vigorously grow both in and out of culture. Regardless of how the various embodiments of the invention work, it is an object of the invention to increase the likelihood of successful initiation.

Methods of Improving Embryogenic Culture Maintenance and Multiplication

Another object of the invention is to improve the efficiency of the maintenance and multiplication steps in conifer somatic embryogenesis. These steps require the vigorous proliferation of embryogenic cultures and the production of numerous somatic embryos. The invention fulfills this objective by providing methods that increase the growth of embryogenic tissues. By "growth," the inventors refer to the survival and proliferation of previously initiated embryogenic cultures. "Growth" can be characterized by any increase in culture size (i.e. area covered on a petri dish), mass, or number of embryos. The growth of embryogenic culture is judged by colony diameters that can be measured using, for example, a dissecting scope ocular micrometer. The "maintenance and multiplication step" refers to the process of growing an embryogenic culture that has been previously initiated in order to provide somatic embryos.

A "previously initiated embryogenic culture" comprises any embryogenic tissue capable of proliferation. Such a culture may consist of an embryogenic mass containing somatic embryos, early pro-embryos and suspensor cells. Such a culture may comprise one or more individual somatic embryos. A previously initiated culture may consist of embryogenic tissues recently formed on an initiation medium. Alternatively, a previously initiated culture can be a subculture of tissues growing on a maintenance media. Alternatively, a previously initiated culture could consist of stored embryogenic tissues or somatic embryos, such as cryopreserved embryos.

The invention encompasses the use of novel culture medium compositions that promote the growth of embryogenic cultures. The invention contemplates that previously initiated embryogenic cultures will be placed on or in a maintenance medium and cultured in order to induce growth. The methods provided by the invention increase the efficiency of the maintenance and multiplication step by providing one or more of the following advantages: more embryos are produced, embryos are produced more rapidly, and a greater number of previously initiated cultures survive to be successfully regenerated into plantlets.

Methods for Improving Embryogenic Culture Capture

The invention also provides methods that improve the efficacy of using liquid multiplication media. The use of liquid multiplication media can be more desirable as it can cost-effectively provide a large number of somatic embryos. The survival and proliferation of previously initiated embryogenic culture transferred to a liquid multiplication media is referred to as liquid culture establishment. The inventors have observed that many initiated cultures have a low survival rate when transferred to liquid multiplication media. For example, the inventors have observed that on average, only 13–33% of initiated cultures of loblolly pine successfully survive and proliferate when transferred to a standard liquid multiplication medium, such as medium 16 shown in Table 1B.

The inventors have further observed that the frequency of capture is strongly related to the starting weight of the tissue transferred to the multiplication media. For example, in experiments on loblolly pine, the majority of nine week-old initiated cultures weighed less than 150 mg and had an average survivorship of about 15%. However, initiated cultures with a mass of 150 mg or greater survived about 80% of the time, and those with a tissue mass of 200 mg or greater survived 88% of the time. We define a culture with an embryo tissue of roughly 200 mg or greater as captured. Thus, the efficiency of using liquid multiplication media is poor at least in part because many of the initiated cultures are too small to survive and proliferate when transferred to liquid multiplication media.

The invention provides methods that increase the frequency of the embryogenic culture capture by at least two means. First, the addition of vitamin $B_{12}$, vitamin E, and organic acids, such as p-aminobenzoic/acid, pyruvic acid and TCA cycle acids (e.g., alpha-ketoglutaratic acid), individually or in combination, to the initiation medium results in improved initiation and a larger embryonic tissue mass as described in Examples 2–5 and 8. Specifically, utilizing the methods of the invention, one can produce an increased proportion of larger cultures, for example, those with a mass of 200 mg or greater. These larger and more robust embryogenic cultures are more likely to survive transfer to a liquid multiplication media. Second, the invention provides methods that increase the frequency of the embryogenic culture capture of the previously initiated tissue by means of the addition of vitamin $B_{12}$, vitamin E, and organic acids, such as p-aminobenzoic acid, pyruvic acid and TCA cycle acids (e.g., alpha-ketoglutaric acid), individually or in combination, to the multiplication medium. The beneficial effects of vitamin $B_{12}$, vitamin E, and organic acids such as alpha-ketoglutaric acid and pyruvic acid on capture of the previously initiated embryogenic tissue are described in Examples 6 and 7.

Suitable Species and Tissues

The present invention is generally suitable for reproducing woody gymnosperms of the order Coniferales. The invention is well suited for propagating trees from species within the families Pinaceae, Cupressaceae, and Taxodiaceae. All species within the genera *Abies, Pinus, Picea, Tsuga, Pseudotsuga, Thuja, Juniperis, Larix, Taxus* and *Sequoia* are amenable to multiplication using the disclosed methods and compositions. For example, the invention is well suited to the *Pinus* species such as *Pinus taeda* (loblolly pine), *Pinus elliottii* (slash pine), *Pinus palustris* (longleaf pine), *Pinus serotina* (pond pine), *Pinus radiata* (Monterey pine), and *Pinus rigida* (pitch pine), as well as other species. In addition, the invention is applicable to hybrids (i.e., interspecies hybrids) of the mentioned pines, including crosses between *Pinus_grigida* and *Pinus taeda*, crosses between *Pinus serotina* and *Pinus taeda*, and reciprocal crosses.

For initiating embryogenic cultures, any conifer tissue explant capable of being employed for somatic embryogenesis is suitable for use in the present invention. A number of explant sources have been used successfully in somatic embryogenesis. These include, but are not limited to, tissue from cotyledons, hypocotyls, epicotyls, buds, meristematic centers from buds or roots, tissues extruded from megagametophytes, and seed embryos. One practicing the invention can use an immature whole megagametophyte containing zygotic embryos or an isolated immature dominant zygotic embryo as the explant. Zygotic embryos removed from seeds can be used. These may or may not include the surrounding gametophyte.

Information further supporting the disclosed invention may be found in the disclosures of U.S. patent application U.S. Ser. No. 09/685,338 and provisional application Ser. No. 60/270,165, herein incorporated by reference.

EXAMPLES

Example 1

Procedures for Culturing Conifer Embryos

Megagametophyte explants were isolated for zygotic initiation tests from loblolly pine summer cones when embryos were at approximately stage 2–4. Seeds were collected from four individual trees of diverse genotypes. Extracted seeds were soaked in running water for 10 minutes, agitated in 10% liquinox supplemented with 2 drops of Tween 20/L (polyoxyethylene-sorbitan monolaurate) for 10 minutes, and rinsed with water for 30 minutes. Seeds were sterilized in a laminar flow hood by agitating in 20% hydrogen peroxide for 10 minutes and rinsing with sterile deionized water. The seed coats, integuments and nucellus were removed to isolate the megagametophytes. Culturing was performed in 24-well culture plates with each well having an approximate volume of 3.0 ml. Two milliliters of media were added into each well. The compositions of the various media used in the examples below are shown in Table 1A–D.

For somatic initiation tests, embryos were selected from a liquid suspension culture supplemented with abscisic acid. (Table 1B, medium 16). Each replication consisted of ten adjacent wells on a multiwell plate, with a single stage 2, somatic embryo per well, providing two replications per multiwell plate. Four replications (for a total of 40 explants) were performed per treatment for each genotype. The plates were wrapped in Parafilm® wrap to minimize evaporation and incubated at 22–24° C. in the dark for 4–6 weeks or until colony diameters were roughly ¾–1 cm. Typically, a single stage 2 embryo is approximately 0.1 mm in size. During this time period, the single embryo multiplies to form an embryogenic tissue mass of about 5–9 mm in diameter depending on the particular conifer, culture genotype, medium contents, and time. Changes in tissue diameters were used to assay the effects of vitamins or organic acid on early-stage embryo growth and multiplication. Colony diameters were measured using a dissecting scope ocular micrometer.

Osmolarity and pH of the culture media were monitored to ensure that these factors were similar throughout various conditions, and therefore, were not contributing to the observed differences. To analyze the results, the ANOVA statistical analysis was performed.

Example 2

Supplementation with K&M Vitamin Mixture for Improved Initiation

K&M vitamin mixture is a solution containing ascorbic acid, biotin, Ca++ Pantotenate, choline chloride, folic acid, myo-inositol, nicotinamide, pyroxidine-HCl, riboflavin, thiamine-HCI, vitamin A (retinol), vitamin $B_{12}$, vitamin D, and p-aminobenzoic acid.

Single somatic embryo initiation tests were conducted to determine the effect of various vitamins on initiation. Embryos of loblolly pine were obtained and treated as described in Example 1. Isolated explants were incubated either in a control medium (Table 1A, medium 1253), or in the same medium supplemented with the K&M vitamin mixture (Table 1A, medium 1335). The final concentrations of the various components of the K&M vitamin mixture in the culture medium are shown in Table 2. Exposure of embryos to the culture medium supplemented with the K&M vitamin mixture lead to an increase in mean colony diameter as compared to the control. Evaluation of specific components of the K&M vitamin mixture lead to identification of the components responsible for the observed increase.

Example 3

Supplementation with Vitamin $B_{12}$ or Vitamin E for Improved Initiation

The inventors have observed that supplementation of vitamins $B_{12}$ and E to culture medium improves initiation in conifer. A representative example is shown for loblolly pine. In this example, the control medium (Table 1A, medium 1253), was tested against the same medium supplemented either with 0.1 mg/L vitamin $B_{12}$ (Table 1A, medium 1357), or vitamin 0.1 mg/L E (Table 1A, medium 1359). The mean colony diameter as measured at 4½ weeks was 15 to 22% greater in the media containing vitamin $B_{12}$ or vitamin E as compared to the control conditions (Table 3).

A further example demonstrates improved initiation and growth in Norway Spruce. Tissue isolated and prepared according to Example 1 was incubated in a medium containing 0.1 mg/L of both vitamin $B_{12}$ and E for 4–5 weeks in the dark at 24–26° C. (Table 1D, medium 1665). Tissue cultured in medium 1665 achieved an average diameter of 3.1 mm compared to tissue cultured in the control medium, which achieved an average diameter of 2.8 mm.

These results demonstrate that improved growth can be attained using media that comprises either vitamin $B_{12}$ or vitamin E. Thus, media supplemented with either vitamin $B_{12}$, or vitamin E, or both, can be used advantageously to increase the yield of initiation in conifer embryogenesis. The concentration of these vitamins in the methods of this invention is between 0.001 and 10 ppm, between 0.01 and 1 ppm, or between 0.1 and 0.5 ppm. The effective concentration may need to be adjusted to the appropriate levels under certain circumstances. For example, the presence of adsorptive agents such as activated charcoal in the media may require higher concentrations of vitamins.

Example 4

Supplementation with an Organic Acid for Improved Initiation

The inventors have observed that the addition of organic acids to a culture medium improves initiation of somatic and zygotic embryos in conifer. Representative organic acids are shown below.

Alpha-ketoglutaric Acid

The addition of alpha-ketoglutaric acid, which is a ketoacid in the TCA cycle, provides a representative example. The inventors have observed that exposure of conifer embryos to alpha-ketoglutaric acid improves initiation.

Single somatic embryo initiation tests were conducted to determine the effect of alpha-ketoglutaric acid on initiation in loblolly pine. Embryos of loblolly pine were obtained and treated as described in Example 1. The inventors note that a modification to the protocol detailed in Example 1 may be required due to the addition of an organic acid to the base medium. The addition of an acid, such as alpha-ketoglutaric acid, causes media pH to drop and therefore, all media supplemented with alpha-ketoglutaric acid were titrated to pH 5.7 before adding them to the cultures. Titration was performed with KOH, which increased potassium levels in the media by about 0.7 mM. The results in such a system demonstrate levels of initiation 20% higher in supplemented culture medium containing 100 ppm alpha-ketoglutaric acid (Table 1B, medium 1342) than in the control medium (Table 1A, medium 1253) as measured by mean colony diameter.

In a related experiment, embryos of loblolly pine were obtained and treated as described in Example 1, except that no $Ca(NO_3)_2.4H_2O$ was present in the culture media initially, but was added at 12 days of incubation. Exposure of embryos to a culture medium that was supplemented with 0.1 mg/L alpha-ketoglutaric acid and K&M vitamin mixture (Table 1A, medium 1381) resulted in an increase of mean colony diameter by 35% as compared to a control medium that did not contain either the K&M vitamin mixture or alpha-ketoglutaric acid (Table 1A, medium 1253), and by 20% as compared to the same medium supplemented with the K&M vitamin mixture (Table 1A, medium 1335).

A further example demonstrating improved initiation with the addition alpha-ketoglutaric acid was conducted with zygotic embryos from Douglas Fir. Embryos of Douglas Fir were obtained, and treated as described in Example 1. The results demonstrate higher levels of initiation in medium supplemented with 100 mg/L alpha-ketoglutaric acid (Table 1D, medium 1624) than initiation in the control medium (Table 1C, medium 121).

These results demonstrate that improved initiation and growth can be attained using culture media that comprises an organic acid such as alpha-ketoglutaric acid. The concentration of the organic acid in the methods of this invention is preferably between 0.01 and 1000 ppm and more preferably between 10 and 500 ppm. However, the effective concentration may need to be adjusted to the appropriate levels under certain circumstances. For example, the presence of adsorptive agents such as activated charcoal in the media may require higher concentrations of the vitamins or the organic acids. Inventors have investigated the impact that the rate of absorption of organic acids may have on the addition of organic acids into a culture medium (data not shown).

Pyruvic Acid

A representative example demonstrating improved initiation in conifer embryos resulting from exposure to pyruvic acid is provided for loblolly pine. Single somatic embryo initiation tests were conducted according to the protocol described in Example 1. The inventors note that modification to the protocol detailed in Example 1 may be required due to the addition of an organic acid to the base medium. In culture medium containing 60.72 mg/L pyruvic acid (Table 1B, medium 1462) mean tissue diameter was 7.1 mm compared to a mean tissue diameter of 6.1 for embryos grown on the control medium 1253 indicating a positive correlation between embryo exposure to pyruvic acid and overall initiation. Iterations of this example in loblolly pine yielded similar percentage increases in initiation, e.g., a 7.2 mm mean tissue diameter for medium containing 0.52 mM pyruvic acid compared to 6.5 mm mean tissue diameter in the control medium. As shown herein, this effect is further enhanced by the combinations of multiple organic acids.

An additional example demonstrating improved initiation with exposure to pyruvic acid is provided for Norway Spruce. Single somatic embryo initiation tests were conducted according to the protocol described in Example 1. The inventors have also tested the addition of sodium pyruvate in addition to pyruvic acid. Results using pyruvic acid are similar to those observed by the inventors for other conifer species. Tissue treatment yielded mean diameters of 3.6 mm for embryos grown in or on medium supplemented with 60.7 mg/L pyruvic acid (Table 1D, medium 1664), compared to mean diameters of 2.8 mm for the control medium (Table 1C, medium 1662). This indicates a stimulatory effect is observed with the addition of 0.52 mM levels of pyruvic acid.

A further example is provided for Douglas Fir. Douglas Fir zygotic embryos were tested for improved initiation when exposed to cultures containing pyruvic acid according to the protocol described in Example 1. Control medium 121 (Table 1C) was supplemented with 60.7 mg/L pyruvic acid to create the test medium (Table 1C, medium 1625). After incubation for eight weeks in the dark, initiation was scored. For tissue exposed to pyruvic acid, mean initiation rates were approximately 35% compared to 32% for the untreated embryos. These results indicate consistency between conifer to demonstrate improved initiation after exposure to pyruvic acid.

p-Aminobenzoic Acid

The inventors have observed that exposure of embryos to organic acids, such as p-aminobenzoic acid improves initiation in conifer.

A representative procedure is shown for loblolly pine, which were obtained and treated as described in Example 1. Embryonic cultures grown on the medium supplemented with 0.2 ppm p-aminobenzoic acid (Table 1A, medium 1434) showed a 32% increase in mean colony diameter as compared to the control (Table 1A, medium 1253).

These results demonstrate that improved initiation and growth can be attained using culture media that comprises p-aminobenzoic acid. The concentration of p-aminobenzoic acid in the methods of this invention is preferably between 0.001 and 100 ppm and more preferably between 0.01 and 10 ppm. However, the effective concentration may need to be adjusted to the appropriate levels under certain circumstances. For example, the presence of adsorptive agents such as activated charcoal in the media may require higher concentrations of p-aminobenzoic acid.

A further representative example in Douglas Fir demonstrates improved initiation when exposing embryos to a culture medium containing p-aminobenzoic acid. When using 20 mg/L p-aminobenzoic acid (Table 1C, medium 1627), 39% initiation is achieved compared to 32% when embryos are cultured in a base medium without p-aminobenzoic acid (Table IC, medium 121).

Example 6

Supplementation with Combination of Vitamin $B_{12}$, Vitamin E, and an Organic Acid for Improved Initiation Zygotic and somatic initiation tests were conducted to determine the effect of alpha-ketoglutaric acid in combination with vitamins $B_{12}$ and E on initiation. Explants of loblolly pine were obtained and treated as described in Example 1 with the following modifications. Each replication consisted of ten adjacent wells on a multiwell plate, with one megagametophyte per well. Ten replications, for a total of 100 seeds, were performed per treatment for each cone collection.

Exposure of explants to a culture medium supplemented with 100 mg/L alpha-ketoglutaric acid, 0.1 mg/L vitamin $B_{12}$, and 0.1 mg/L vitamin E (Table 1B, medium 1391) resulted in a higher extrusion and initiation efficiency as compared to control medium 1253. Specifically, in comparison to the control, average extrusion across four cone collections increased from 67% to 71% and average initiation across four cone collections increased from 38% to 43%. The medium containing 0.1 mg/L vitamin $B_{12}$ (Table 1A, medium 1357) or 0.1 mg/L vitamin E (Table 1A, medium 1359) showed some, but a lesser effect. Early extrusion and embryo expansion were more robust with vitamin E or alpha-ketoglutaric acid present.

An additional example in Slash Pine demonstrates the stimulatory effects that vitamins $B_{12}$ and E and an organic acid have on zygotic initiation. Exposure of the megagametophytes to culture medium supplemented with 100 mg/L alpha-ketoglutaric acid, 0.1 mg/L, vitamin $B_{12}$ and 0.1 mg/L vitamin E (Table 1B, medium 1391) resulted in increases in initiation rates. After culturing for eight weeks in the dark, initiation rates achieved a mean of roughly 29% in medium 1391 compared to roughly 23% in a medium without vitamins and alpha-ketoglutaric acid (Table 1A, medium 1253). The addition of 60.7 mg/L pyruvic acid, 0.1 mg/L vitamin B12 and 0.1 mg/L vitamin E also produced higher general average initiation in Slash Pine.

Comparable results were further observed in Norway Spruce using a somatic embryos as prepared by methods shown in Example 1 using a medium with a combination of alpha-ketoglutaric acid and vitamins $B_{12}$ and E (Table 1D, medium 1666).

The inventors have found that the presence of multiple organic acids, such as alpha-ketoglutaric acid and pyruvic acid, and vitamins $B_{12}$ and E in a culture medium further improve initiation. According to the protocol of Example 1, four loblolly pine cone collections of approximately 500 seeds per collection with embryos at stages 2–4 were selected. Seeds were sterilized and dissected. The integuments and nucellus were removed and the megagametophytes was placed onto both test medium 1592 containing 100 mg/L alpha-ketoglutaric acid and 60.7 mg/L pyruvic acid (Table 1D) and control medium 1253 (Table 1A) for an eight week incubation in the dark. Average initiation across the cone collections was roughly 30% for embryos grown on the control medium and roughly 36% for embryos grown on the test medium.

These results demonstrate that higher extrusion and improved initiation can be attained using culture media that comprises $B_{12}$, vitamin E and an organic acid, such as alpha-ketoglutaric acid, individually or in combination. The concentration of $B_{12}$ or vitamin E in this embodiment of the invention is between 0.001 and 10 ppm, between 0.01 and 1 ppm, or between 0.1 and 0.5 ppm. The concentration of alpha-ketoglutaric acid in this embodiment of the invention is preferably between 0.01 and 1000 ppm and more preferably between 10 and 500 ppm. The effective concentrations may need to be adjusted to the appropriate levels under certain circumstances as described above.

Example 7

Supplementation with an Organic Acid for Improved Capture

Tests were conducted to determine the effect on somatic embryo capture of a medium supplemented with individual organic acids, such as alpha-ketoglutaric acid. Embryos of loblolly pine were obtained and treated as described in Example 1. Individual stage 2 embryos were selected from liquid maintenance medium and placed in multiplication medium (Table 1B, medium 1250).

When alpha-ketoglutaric acid was the only additive to the control medium (Table 1B, medium 1250), a 5–6% increase in mean colony diameter was observed at alpha-ketoglutaric acid concentrations between 100 and 200 mg/L.

These results demonstrate that improved somatic embryo capture can be attained using culture media that comprises an organic acid, such as alpha-ketoglutaric acid. The concentration of the organic acid in the methods of this invention is preferably between 0.01 and 1000 ppm and more preferably between 10 and 500 ppm. The effective concentration may need to be adjusted to the appropriate levels under certain circumstances as described above.

An additional example demonstrating improved somatic capture is provided for medium supplemented with pyruvic acid. Embryos of loblolly pine were obtained and treated as described in Example 1. Individual stage 2 embryos were selected from liquid maintenance medium and placed in multiplication medium (Table 1B, medium 1250). Stage 2 embryos were likewise placed in medium 1250 supplemented with 60.7 mg/L pyruvic acid (Table 1C, medium 1635). All cultures were incubated in the dark at 24–26° C. for 4–5 weeks. Results demonstrated improved growth for embryos exposed to pyruvic acid. For example, one study indicates that the average diameter embryos grown in medium 1635 measure roughly 3.7 mm in diameter, while embryos grown in control medium 1250 were 3.3 mm in diameter.

Example 8

Supplementation with Combination of Vitamin $B_{12}$, Vitamin E and an Organic Acid for Improved Capture Tests were conducted to determine the effect of a combination of a TCA cycle acid, such as alpha-ketoglutaric acid, vitamin $B_{12}$, and vitamin E on somatic embryo capture. The inventors have observed improved capture rates using a culture medium supplemented with an individual organic acid such as alpha-ketoglutaric acid, vitamin $B_{12}$, and vitamin E, or supplemented with a combination of organic acids, such as alpha-ketoglutaric acid and pyruvic acid, and vitamins $B_{12}$ and E.

A representative example for somatic capture uses embryos of loblolly pine obtained and treated as described in Example 1. Individual stage 2 embryos were selected from liquid maintenance medium and placed in multiplication medium (Table 1B, medium 1250). Compared to this control, the addition of 0.1 mg/L vitamin $B_{12}$ alone to the multiplication medium (Table 1B, medium 1250) increased mean colony diameter by approximately 5%. Likewise, the addition of 100 mg/L alpha-ketoglutaric acid alone to the maintenance medium (Table 1B, medium 1250) increased mean colony diameter by approximately 10%. When the media were supplemented with 0.1 mg/L vitamin $B_{12}$, 0.1 mg/L vitamin E, and 100 mg/L alpha-ketoglutaric acid (Table 1B, medium 1409), the increase in mean colony diameter was approximately 12% over the control medium (Table 1 B, medium 1250).

These results demonstrate that improved somatic embryo capture can be attained using culture medium that comprises $B_{12}$, vitamin E, or an organic acid, such alpha-ketoglutaric acid, individually or in combination. The concentration of vitamin $B_{12}$ or vitamin E in the methods of this invention is between 0.001 and 10 ppm, between 0.01 and 1 ppm, or between 0.1 and 0.5 ppm. The concentration of alpha-ketoglutaric acid in the methods of this invention is between 0.01 and 1000 ppm or between 10 and 500 ppm. The effective concentrations need to be adjusted to the appropriate levels under certain circumstances as described above.

A further representative example demonstrating improved somatic capture with a combination of organics acids and vitamins $B_{12}$ and E uses embryos of loblolly pine obtained and treated as described in Example 1. Individual stage 2 embryos were selected from liquid maintenance medium and placed in multiplication control medium (Table 1B, medium 1250), as well as medium 1638, which is supplemented with 0.1 mg/L vitamin $B_{12}$, 0.1 mg/L vitamin E, 100 mg/L alpha-ketoglutaric acid and 60.7 mg/L pyruvic acid (Table 1C, medium 1638). Compared to embryos incubated in the control medium, the mean colony diameter increased for the supplement medium from roughly 3.3 mm to 4.2 mm. This demonstrates that combinations of organic acids may have additional benefits beyond the stimulatory effects observed for individual organic acids.

TABLE 1A

MEDIA COMPOSITIONS

| COMPONENTS (mg/L) | 1253 | 1335 | 1381 | 1357 | 1359 | 1434 |
|---|---|---|---|---|---|---|
| $NH_4NO_3$ | 200.0 | 200.0 | 200.0 | 200.0 | 200.0 | 200.0 |
| $KNO_3$ | 909.9 | 909.9 | 909.9 | 909.9 | 909.9 | 909.9 |
| $KH_2PO_4$ | 136.1 | 136.1 | 136.1 | 136.1 | 136.1 | 136.1 |
| $Ca(NO_3)_2 \cdot 4H_2O$ | 236.2 | 236.2 | 236.2 | 236.2 | 236.2 | 236.2 |
| $MgSO_4 \cdot 7H_2O$ | 246.5 | 246.5 | 246.5 | 246.5 | 246.5 | 246.5 |
| $Mg(NO_3)_2 \cdot 6H_2O$ | 256.5 | 256.5 | 256.5 | 256.5 | 256.5 | 256.5 |
| $MgCl_2 \cdot 6H_2O$ | 101.7 | 101.7 | 101.7 | 101.7 | 101.7 | 101.7 |
| KI | 4.15 | 4.15 | 4.15 | 4.15 | 4.15 | 4.15 |
| $H_3BO_3$ | 15.5 | 15.5 | 15.5 | 15.5 | 15.5 | 15.5 |
| $MnSO_4 \cdot H_2O$ | 10.5 | 10.5 | 10.5 | 10.5 | 10.5 | 10.5 |
| $ZnSO_4 \cdot 7H_2O$ | 14.67 | 14.67 | 14.67 | 14.67 | 14.67 | 14.67 |
| $NaMoO_4 \cdot 2H_2O$ | 0.125 | 0.125 | 0.125 | 0.125 | 0.125 | 0.125 |
| $CuSO_4 \cdot 5H_2O$ | 0.1725 | 0.1725 | 0.1725 | 0.1725 | 0.1725 | 0.1725 |
| $CoCl_2 \cdot 6H_2O$ | 0.125 | 0.125 | 0.125 | 0.125 | 0.125 | 0.125 |
| $AgNO_3$ | 3.4 | 3.4 | 3.4 | 3.4 | 3.4 | 3.4 |
| $FeSO_4 \cdot 7H_2O$ | 13.9 | 13.9 | 13.9 | 13.9 | 13.9 | 13.9 |
| $Na_2EDTA$ | 18.65 | 18.65 | 18.65 | 18.65 | 18.65 | 18.65 |
| Maltose | 15,000 | 15,000 | 15,000 | 15,000 | 15,000 | 15,000 |
| myo-Inositol | 20,000 | 20,000* | 20,000* | 20,000 | 20,000 | 20,000 |
| MES | 250 | 250 | 250 | 250 | 250 | 250 |
| Biotin (ppm) | 0.05 | 0.05* | 0.05* | 0.05 | 0.05 | 0.05 |
| Folic Acid (ppm) | 0.5 | 0.5* | 0.5* | 0.5 | 0.5 | 0.5 |
| Casamino Acids | 500 | 500 | 500 | 500 | 500 | 500 |
| L-Glutamine | 450 | 450 | 450 | 450 | 450 | 450 |
| Thiamine.HCl | 1.0 | 1.0* | 1.0* | 1.0 | 1.0 | 1.0 |
| Pyridoxine.HCL | 0.5 | 0.5* | 0.5* | 0.5 | 0.5 | 0.5 |
| Nicotinic acid | 0.5 | 0.5* | 0.5* | 0.5 | 0.5 | 0.5 |
| Glycine | 2.0 | 2.0 | 2.0 | 2.0 | 2.0 | 2.0 |
| NAA | 2.0 | 2.0 | 2.0 | 2.0 | 2.0 | 2.0 |
| BAP | 0.63 | 0.63 | 0.63 | 0.63 | 0.63 | 0.63 |
| Kinetin | 0.61 | 0.61 | 0.61 | 0.61 | 0.61 | 0.61 |

TABLE 1A-continued

MEDIA COMPOSITIONS

| COMPONENTS (mg/L) | Media | | | | | |
|---|---|---|---|---|---|---|
| | 1253 | 1335 | 1381 | 1357 | 1359 | 1434 |
| Activated Charcoal | 50 | 50 | 50 | 50 | 50 | 50 |
| CGMP ($\mu$M) | 10 | 10 | 10 | 10 | 10 | 10 |
| Gelrite | 2,000 | 2,000 | 2,000 | 2,000 | 2,000 | 2,000 |
| Brassinolide ($\mu$M) | 0.1 | 0.1 | 0.1 | 0.1 | 0.1 | 0.1 |
| K&M vitamins | — | 1× | 1× | — | — | — |
| Vitamin $B_{12}$ (ppm) | — | — | — | 0.1 | — | — |
| Vitamin E (ppm) | — | — | — | — | 0.1 | — |
| Alpha-ketoglutarate | — | — | 100 | — | — | — |
| p-aminobenzoate (ppm) | — | — | — | — | — | 0.2 |
| pH titrated to | 5.7 | 5.7 | 5.7 | 5.7 | 5.7 | 5.7 |

TABLE 1B

MEDIA COMPOSITIONS

| COMPONENTS (mg/L) | M dia | | | | | |
|---|---|---|---|---|---|---|
| | 16 | 1250 | 1342 | 1391 | 1409 | 1462 |
| $NH_4NO_3$ | 603.8 | 603.8 | 200.0 | 200.0 | 603.8 | 200.0 |
| $KNO_3$ | 909.9 | 909.9 | 909.9 | 909.9 | 909.9 | 909.9 |
| $KH_2PO_4$ | 136.1 | 136.1 | 136.1 | 136.1 | 136.1 | 136.1 |
| $Ca(NO_3)_2 \cdot 4H_2O$ | 236.2 | 236.2 | 236.2 | 236.2 | 236.2 | 236.2 |
| $MgSO_4 \cdot 7H_2O$ | 246.5 | 246.5 | 246.5 | 246.5 | 246.5 | 246.5 |
| $Mg(NO_3)_2 \cdot 6H_2O$ | 256.5 | 256.5 | 256.5 | 256.5 | 256.5 | 256.5 |
| $MgCl_2 \cdot 6H_2O$ | 101.7 | 101.7 | 101.7 | 101.7 | 101.7 | 101.7 |
| KI | 4.15 | 4.15 | 4.15 | 4.15 | 4.15 | 4.15 |
| $H_3BO_3$ | 15.5 | 15.5 | 15.5 | 15.5 | 15.5 | 15.5 |
| $MnSO_4 \cdot H_2O$ | 10.5 | 10.5 | 10.5 | 10.5 | 10.5 | 10.5 |
| $ZnSO_4 \cdot 7H_2O$ | 14.4 | 14.4 | 14.67 | 14.67 | 14.4 | 14.67 |
| $NaMoO_4 \cdot 2H_2O$ | 0.125 | 0.125 | 0.125 | 0.125 | 0.125 | 0.125 |
| $CuSO_4 \cdot 5H_2O$ | 0.125 | 0.125 | 0.1725 | 0.1725 | 0.125 | 0.1725 |
| $CoCl_2 \cdot 6H_2O$ | 0.125 | 0.125 | 0.125 | 0.125 | 0.125 | 0.125 |
| $AgNO_3$ | — | — | 3.4 | 3.4 | — | 3.4 |
| $FeSO_4 \cdot 7H_2O$ | 6.95 | 6.95 | 13.9 | 13.9 | 6.95 | 13.9 |
| $Na_2EDTA$ | 9.33 | 9.33 | 18.65 | 18.65 | 9.33 | 18.65 |
| Sucrose | 30,000 | 30,000 | 15,000 | — | 30,000 | — |
| Maltose | — | — | 20,000 | 15,000 | — | 15,000 |
| myo-Inositol | 1,000 | 1,000 | 250 | 20,000 | 1,000 | 20,000 |
| MES | — | 250 | 0.05 | 250 | 250 | 250 |
| Biotin (ppm) | 0.05 | 0.05 | 0.5 | 0.05 | 0.05 | 0.05 |
| Folic Acid (ppm) | 0.5 | 0.5 | 500 | 0.5 | 0.5 | 0.5 |
| α-Ketoglutarate Acid | — | — | 100 | — | — | — |
| Pyruvic acid | — | — | 1.0 | — | — | 60.72 |
| Casamino Acids | 500 | 500 | 0.5 | 500 | 500 | 500 |
| L-Glutamine | 450 | 450 | 0.5 | 450 | 450 | 450 |
| Thiamine.HCL | 1.0 | 1.0 | 2.0 | 1.0 | 1.0 | 1.0 |
| Pyridoxine.HCL | 0.5 | 0.5 | 2.0 | 0.5 | 0.5 | 0.5 |
| Nicotinic acid | 0.5 | 0.5 | 0.63 | 0.5 | 0.5 | 0.5 |
| Glycine | 2.0 | 2.0 | 0.61 | 2.0 | 2.0 | 2.0 |
| NAA | — | — | 50 | 2.0 | — | 2.0 |
| Abscisic Acid | — | 1.3 | 10 | — | 1.3 | — |
| 2,4 D | 1.1 | 1.1 | 2,000 | — | 1.1 | — |
| BAP | 0.45 | 0.45 | 0.1 | 0.63 | 0.45 | 0.63 |
| Kinetin | 0.43 | 0.43 | — | 0.61 | 0.43 | 0.61 |
| Activated Charcoal | — | — | — | 50 | — | 50 |
| CGMP ($\mu$M) | — | — | — | 10 | — | 10 |
| Gelrite | — | 2,000 | 100 | 2,000 | 2,000 | 2,000 |
| Brassinolide ($\mu$M) | — | — | — | 0.1 | — | 0.1 |
| Vitamin $B_{12}$ (ppm) | — | — | 5.7 | 0.1 | 0.1 | — |
| Vitamin E (ppm) | — | — | — | — | 0.1 | — |
| Alpha-ketoglutarate | — | — | — | 100 | 100 | — |
| p-aminobenzoate (ppm) | — | — | — | — | — | — |
| pH titrated to | 5.7 | 5.7 | 5.7 | 5.7 | 5.7 | 5.7 |

TABLE 1C

MEDIA COMPOSITIONS

| COMPONENTS | Media | | | | | |
|---|---|---|---|---|---|---|
| (mg/L) | 121 | 1625 | 1627 | 1635 | 1638 | 1662 |
| $NH_4NO_3$ | — | — | — | 603.8 | 603.8 | 206.3 |
| $KNO_3$ | 1250 | 1250 | 1250 | 909.9 | 909.9 | 2340 |
| $KH_2PO_4$ | 340 | 340 | 340 | 136.1 | 136.1 | 85 |
| $Ca(NO_3)_2.4H_2O$ | — | — | — | 236.2 | 236.2 | — |
| $CaCl_2.2H_2O$ | 200 | 200 | 200 | — | — | 220 |
| $MgSO_4.7H_2O$ | 400 | 400 | 400 | 246.5 | 246.5 | 185 |
| $Mg(NO_3)_2.6H_2O$ | — | — | — | 256.5 | 256.5 | — |
| $MgCl_2.6H_2O$ | — | — | — | 101.7 | 101.7 | — |
| KI | 1.0 | 1.0 | 1.0 | 4.15 | 4.15 | 0.415 |
| $H_3BO_3$ | 5.0 | 5.0 | 5.0 | 15.5 | 15.5 | 3.1 |
| $MnSO_4.H_2O$ | 20.8 | 20.8 | 20.8 | 10.5 | 10.5 | 8.45 |
| $ZnSO_4.7H_2O$ | 8.0 | 8.0 | 8.0 | 14.4 | 14.4 | 4.3 |
| $NaMoO_4.2H_2O$ | 0.2 | 0.2 | 0.2 | 0.125 | 0.125 | 0.125 |
| $CuSO_4.5H_2O$ | 0.025 | 0.025 | 0.025 | 0.125 | 0.125 | 0.0125 |
| $CoCl_2.6H_2O$ | 0.025 | 0.025 | 0.025 | 0.125 | 0.125 | 0.0125 |
| $FeSO_4.7H_2O$ | 27.8 | 27.8 | 27.8 | 9.95 | 9.95 | 13.9 |
| $Na_2EDTA$ | 37.3 | 37.3 | 37.3 | 9.33 | 9.33 | 18.65 |
| MES | — | — | — | 250 | 250 | — |
| Sucrose | 15,000 | 15,000 | 15,000 | 30,000 | 30,000 | 30,000 |
| myo-Inositol | 1,000 | 1,000 | 1,000 | 1,000 | 1,000 | 1,000 |
| Pyruvic acid | — | 60.7 | — | 60.7 | 60.7 | — |
| Vitamin E (ppm) | — | — | — | — | 0.1 | — |
| Vitamin $B_{12}$ (ppm) | — | — | — | — | 0.1 | — |
| Thiamine.HCL | 1.0 | 1.0 | 1.0 | 1.0 | 1.0 | 0.1 |
| Pyridoxine.HCL | 0.5 | 0.5 | 0.5 | 0.5 | 0.5 | 0.5 |
| Nicotinic acid | 0.5 | 0.5 | 0.5 | 0.5 | 0.5 | 0.5 |
| L-Glutamine | — | — | — | 450 | 450 | 450 |
| Casamino Acids | 500 | 500 | 500 | 500 | 500 | 500 |
| ABA | 0 | 0 | 0 | — | — | — |
| Brassinolide (μM) | 0 | 0 | 0 | — | — | — |
| Activated Charcoal | 2,500 | 2,500 | 2,500 | — | — | — |
| Glycine | 2.0 | 2.0 | 2.0 | 2.0 | 2.0 | 2.0 |
| Biotin | — | — | — | 0.05 | 0.05 | — |
| Folic Acid | — | — | — | 0.5 | 0.5 | — |
| Abscisic Acid | — | — | — | 1.3 | 1.3 | — |
| α-Ketoglutarate | — | — | — | — | 100 | — |
| Pyruvic Acid | — | — | — | — | 60.7 | — |
| BAP | 45 | 45 | 45 | 0.45 | 0.45 | 0.045 |
| Kinetin | 43 | 43 | 43 | 0.43 | 0.43 | 0.043 |
| 2,4 D | 110 | 110 | 110 | 1.1 | 1.1 | 0.11 |
| Gelrite | 2,000 | 2,000 | 2,000 | 2,500 | 2,500 | 2,500 |
| pH titrated to | 5.7 | 5.7 | 5.7 | 5.7 | 5.7 | 5.7 |

TABLE 1D

MEDIA COMPOSITIONS

| COMPONENTS | Media | | | | |
|---|---|---|---|---|---|
| (mg/L) | 1592 | 1624 | 1664 | 1665 | 1666 |
| $NH_4NO_3$ | 200.0 | — | 206.3 | 206.3 | 206.3 |
| $KNO_3$ | 909.9 | 1250 | 2340 | 2340 | 2340 |
| $KH_2PO_4$ | 136.1 | 340 | 85 | 85 | 85 |
| $Ca(NO_2)_24H_2O$ | 236.2 | | | | |
| $CaCl_2.2H_2O$ | — | 200 | 220 | 220 | 220 |
| $MgSO_4.7H_2O$ | 246.5 | 400 | 185 | 185 | 185 |
| $Mg(NO_3)_2.6H_2O$ | 256.5 | | — | — | — |
| $MgCl_2.6H_2O$ | 101.7 | | — | — | — |
| KI | 4.15 | 1.0 | 0.415 | 0.415 | 0.415 |
| $H_3BO_3$ | 15.5 | 5.0 | 3.1 | 3.1 | 3.1 |
| $MnSO_4.H_2O$ | 10.5 | 20.8 | 8.45 | 8.45 | 8.45 |
| $ZnSO_4.7H_2O$ | 14.67 | 8.0 | 4.3 | 4.3 | 4.3 |
| $NaMoO_4.2H_2O$ | 0.125 | 0.2 | 0.125 | 0.125 | 0.125 |
| $CuSO_4.5H_2O$ | 0.1725 | 0.025 | 0.0125 | 0.0125 | 0.0125 |
| $CoCl_2.6H_2O$ | 0.125 | 0.025 | 0.0125 | 0.0125 | 0.0125 |
| $AgNO_3$ | 3.398 | | — | — | — |
| $FeSO_4.7H_2O$ | 13.9 | 27.8 | 13.9 | 13.9 | 13.9 |
| $Na_2EDTA$ | 18.65 | 37.3 | 18.65 | 18.65 | 18.65 |
| Sucrose | — | 15,000 | 30,000 | 30,000 | 30,000 |

TABLE 1D-continued

MEDIA COMPOSITIONS

| COMPONENTS (mg/L) | Media 1592 | 1624 | 1664 | 1665 | 1666 |
|---|---|---|---|---|---|
| Maltose | 15,000 | — | — | — | — |
| MES | 250 | — | — | — | — |
| Biotin | 0.05 | — | — | — | — |
| Folic Acid | 0.5 | — | — | — | — |
| myo-Inositol | 20,000 | 1,000 | 1,000 | 1,000 | 1,000 |
| Pyruvic acid | 60.7 | — | 60.7 | — | — |
| Vitamin E (ppm) | 0.1 | — | — | 0.1 | 0.1 |
| Vitamin $B_{12}$ (ppm) | 0.1 | — | — | 0.1 | 0.1 |
| Thiamine.HCL | 0.1 | 0.1 | 0.1 | 0.1 | 0.1 |
| Pyridoxine.HCL | 0.5 | 0.5 | 0.5 | 0.5 | 0.5 |
| Nicotinic acid | 0.5 | 0.5 | 0.5 | 0.5 | 0.5 |
| L-Glutamine | 450 | — | 450 | 450 | 450 |
| Casamino Acids | 500 | 500 | 500 | 500 | 500 |
| ABA | — | 0 | — | — | — |
| Brassinolide ($\mu$M) | 0.1 | 0 | — | — | — |
| Activated Charcoal | 50 | 2,500 | — | — | — |
| Glycine | 2.0 | 2.0 | 2.0 | 2.0 | 2.0 |
| BAP | 0.63 | 45 | 0.045 | 0.045 | 0.045 |
| cGMP($\mu$M) | 10 | — | — | — | — |
| Kinetin | 0.61 | 43 | 0.043 | 0.043 | 0.043 |
| $\alpha$-Ketoglutarate | — | 100 | — | — | 100 |
| 2,4 D | — | 110 | 0.11 | 0.11 | 0.11 |
| Gelrite | 2,000 | 2,000 | 2,500 | 2,500 | 2,500 |
| pH titrated to | 5.7 | 5.7 | 5.7 | 5.7 | 5.7 |

TABLE 2

FINAL CONCENTRATIONS OF THE K&M VITAMIN MIXTURE COMPONENTS

| Component | Final Concentration (ppm) |
|---|---|
| Ascorbic Acid | 2.0 |
| Biotin | 0.01 |
| Ca++ Pantotenate | 1.0 |
| Choline Chloride | 1.0 |
| Folic Acid | 0.4 |
| Myo-Inositol | 100.0 |
| Nincotinamide | 1.0 |
| Pyroxidine-HCl | 1.0 |
| Riboflavin | 0.2 |
| Thiamine-HCl | 1.0 |
| Vitamin A | 0.01 |
| Vitamin $B_{12}$ | 0.02 |
| Vitamin D | 0.01 |
| p-aminobenzoic acid | 0.02 |

TABLE 3

MEAN COLONY DIAMETER BY TREATMENT WITH VITAMINS $B_{12}$ AND E

| Treatment | Mean Colony Diameter (mm) |
|---|---|
| Control (medium 1253) | 4.00 |
| + vitamin $B_{12}$ (medium 1357) | 4.88 |
| + vitamin E (medium 1359) | 4.65 |

The specification is most thoroughly understood in light of the teachings of the references cited within the specification, all of which are hereby incorporated by reference in their entirety. The embodiments within the specification provide an illustration of embodiments of the invention and should not be construed to limit the scope of the invention. The skilled artisan recognizes that many other embodiments are encompassed by the claimed invention and that it is intended that the specification and examples be considered as exemplary only, with a true scope and spirit of the invention being indicated by the following claims.

What is claimed is:

1. A method of initiating conifer somatic embryogenic cultures comprising a step of culturing explants using a medium comprising vitamin E.

2. The method of claim 1, wherein the concentration of vitamin E is from 0.001 to 10 ppm.

3. The method of claim 1, wherein the concentration of vitamin E is from 0.01 to 1 ppm.

4. The method of claim 1, wherein the concentration of vitamin E is from 0.1 to 0.5 ppm.

5. A method of initiating conifer somatic embryogenic cultures comprising a step of culturing explants using a medium comprising vitamin $B_{12}$.

6. The method of claim 5, wherein the concentration of vitamin $B_{12}$ is from 0.001 to 10 ppm.

7. The method of claim 5, wherein the concentration of vitamin $B_{12}$ is from 0.01 to 1 ppm.

8. The method of claim 5, wherein the concentration of vitamin $B_{12}$ is from 0.1 to 0.5 ppm.

9. A method of initiating conifer somatic embryogenic cultures comprising a step of culturing explants using a medium comprising an organic acid, wherein said acid is not abscisic acid or p-amino-benzoic acid.

10. The method of claim 9, wherein said organic acid is a TCA cycle acid.

11. The method of claim 10, wherein said TCA cycle acid is alpha-ketoglutaric acid.

12. The method of claim 11, wherein the concentration of alpha-ketoglutaric acid is from 0.01 to 1000 ppm.

13. The method of claim 11, wherein the concentration of alpha-ketoglutaric acid is from 10 to 500 ppm.

14. The method of claim 9, wherein said organic acid is pyruvic acid.

15. The method of claim 14, wherein the concentration of pyruvic acid is from 0.01 to 1000 ppm.

16. The method of claim 14, wherein the concentration of pyruvic acid is from 10 to 500 ppm.

17. A method of growing previously initiated conifer somatic embryogenic tissues, comprising the step of culturing said tissues in a medium comprising vitamin E.

18. The method of claim 17, wherein the concentration of vitamin E is from 0.001 to 10 ppm.

19. The method of claim 17, wherein the concentration of vitamin E is from 0.01 to 1 ppm.

20. The method of claim 17, wherein the concentration of vitamin E is from 0.1 to 0.5 ppm.

21. A method of growing previously initiated conifer somatic embryogenic tissues, comprising the step of culturing said tissues in a medium comprising vitamin $B_{12}$.

22. The method of claim 21, wherein the concentration of vitamin $B_{12}$ is from 0.001 to 10 ppm.

23. The method of claim 21, wherein the concentration of vitamin $B_{12}$ is from 0.01 to 1 ppm.

24. The method of claim 21, wherein the concentration of vitamin $B_{12}$ is from 1.0 to 10 ppm.

25. A method of growing previously initiated conifer somatic embryogenic tissues, comprising the step of culturing said tissues in a medium comprising an organic acid, wherein said acid is not absoisic acid or p-amino-benzoic acid.

26. The method claim 25, wherein said organic acid is a TCA cycle acid.

27. The method of claim 26, wherein said TCA cycle acid is alpha-ketoglutaric acid.

28. The method of claim 26, wherein the concentration of alpha-ketoglutaric acid is from 0.01 to 1000 ppm.

29. The method of claim 26, wherein the concentration of alpha-ketoglutaric acid is from 10 to 500 ppm.

30. The method of claim 25, wherein said organic acid is pyruvic acid.

31. The method of claim 30, wherein the concentration of pyruvic acid is from 0.01 to 1000 ppm.

32. The method of claim 30, wherein the concentration of pyruvic acid is from 10 to 500 ppm.

* * * * *